(12) United States Patent
Lechmann et al.

(10) Patent No.: US 8,709,085 B2
(45) Date of Patent: *Apr. 29, 2014

(54) INTERVERTEBRAL IMPLANT

(75) Inventors: Beat Lechmann, Langendorf (CH); Dominique Burkard, Gretzenbach (CH); Claude Mathieu, Zurich (CH); Christopher Marden John Cain, Norwood (AU)

(73) Assignee: DePuy Synthes Products, LLC, Raynham, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 13/284,650

(22) Filed: Oct. 28, 2011

(65) Prior Publication Data

US 2012/0101580 A1    Apr. 26, 2012

Related U.S. Application Data

(63) Continuation of application No. 12/969,330, filed on Dec. 15, 2010, which is a continuation of application No. 12/432,088, filed on Apr. 29, 2009, now Pat. No. 7,862,616, which is a continuation of application No. 11/199,599, filed on Aug. 8, 2005, now Pat. No. 7,846,207, which is a continuation of application No. PCT/CH03/00089, filed on Feb. 6, 2003.

(51) Int. Cl.
*A61F 2/44* (2006.01)
(52) U.S. Cl.
USPC .................... 623/17.16; 623/17.11
(58) Field of Classification Search
USPC ............................ 623/17.11–17.16
See application file for complete search history.

(56) References Cited

U.S. PATENT DOCUMENTS

| 1,105,105 A | 7/1914 | Sherman |
| 2,621,145 A | 12/1952 | Sano |
| 4,135,506 A | 1/1979 | Ulrich |
| 4,501,269 A | 2/1985 | Bagby |
| 4,503,848 A | 3/1985 | Caspar et al. |
| 4,512,038 A | 4/1985 | Alexander et al. |
| 4,599,086 A | 7/1986 | Doty |
| 4,627,853 A | 12/1986 | Campbell et al. |
| 4,678,470 A | 7/1987 | Nashef et al. |

(Continued)

FOREIGN PATENT DOCUMENTS

| CA | 2317791 | 8/1999 |
| DE | 3042003 | 7/1982 |

(Continued)

OTHER PUBLICATIONS

International Patent Application No. PCT/CH2003/00089, International Search Report, dated Dec. 3, 2003, 3 pages.

(Continued)

*Primary Examiner* — Pedro Philogene
*Assistant Examiner* — Lynnsy Schneider
(74) *Attorney, Agent, or Firm* — Baker & Hostetler LLP

(57) ABSTRACT

An intervertebral implant includes a three-dimensional body and a securing plate. The three-dimensional body includes a front surface and a rear surface. The three-dimensional body further includes a plurality of boreholes for accommodating fixation elements. The intervertebral implant also includes a front plate disposed at the front surface of the three-dimensional body and having a plurality of boreholes. A securing plate can be fastened to the front plate.

58 Claims, 6 Drawing Sheets

(56) References Cited

U.S. PATENT DOCUMENTS

| | | |
|---|---|---|
| 4,717,115 A | 1/1988 | Schmitz et al. |
| 4,858,603 A | 8/1989 | Clemow et al. |
| 4,904,261 A | 2/1990 | Dove et al. |
| 4,936,851 A | 6/1990 | Fox et al. |
| 4,950,296 A | 8/1990 | McIntyre |
| 4,955,908 A | 9/1990 | Frey et al. |
| 4,961,740 A | 10/1990 | Ray et al. |
| 4,978,350 A | 12/1990 | Wagenknecht |
| 4,994,084 A | 2/1991 | Brennan |
| 5,026,373 A | 6/1991 | Ray et al. |
| 5,053,049 A | 10/1991 | Campbell |
| 5,062,850 A | 11/1991 | MacMillan et al. |
| 5,084,051 A | 1/1992 | Tormala et al. |
| 5,085,660 A | 2/1992 | Lin |
| 5,112,354 A | 5/1992 | Sires |
| 5,180,381 A | 1/1993 | Aust et al. |
| 5,192,327 A | 3/1993 | Brantigan |
| 5,211,664 A | 5/1993 | Tepic et al. |
| 5,235,034 A | 8/1993 | Bobsein et al. |
| 5,275,601 A | 1/1994 | Gogolewski et al. |
| 5,281,226 A | 1/1994 | Davydov et al. |
| 5,284,655 A | 2/1994 | Bogdansky et al. |
| 5,290,312 A | 3/1994 | Kojimoto et al. |
| 5,298,254 A | 3/1994 | Prewett et al. |
| 5,314,476 A | 5/1994 | Prewett et al. |
| 5,314,477 A | 5/1994 | Marnay |
| 5,348,788 A | 9/1994 | White |
| 5,397,364 A * | 3/1995 | Kozak et al. ............. 623/17.11 |
| 5,405,391 A | 4/1995 | Hednerson et al. |
| 5,423,817 A | 6/1995 | Lin |
| 5,439,684 A | 8/1995 | Prewett et al. |
| 5,458,638 A | 10/1995 | Kuslich et al. |
| 5,458,641 A | 10/1995 | Ramirez |
| 5,489,308 A | 2/1996 | Kuslich et al. |
| 5,507,818 A | 4/1996 | McLaughlin |
| 5,514,180 A | 5/1996 | Heggeness et al. |
| 5,520,690 A | 5/1996 | Errico et al. |
| 5,522,899 A | 6/1996 | Michelson |
| 5,531,746 A | 7/1996 | Errico et al. |
| 5,534,030 A | 7/1996 | Navarro et al. |
| 5,534,031 A | 7/1996 | Matsuzaki et al. |
| 5,549,612 A | 8/1996 | Yapp et al. |
| 5,549,679 A | 8/1996 | Kuslich |
| 5,554,191 A | 9/1996 | Lahille et al. |
| 5,556,430 A | 9/1996 | Gendler |
| 5,569,308 A | 10/1996 | Sottosanti |
| 5,571,190 A | 11/1996 | Ulrich et al. |
| 5,571,192 A | 11/1996 | Schonhoffer |
| 5,593,409 A | 1/1997 | Michelson |
| 5,601,553 A | 2/1997 | Trebing et al. |
| 5,607,474 A | 3/1997 | Athanasiou et al. |
| 5,609,635 A * | 3/1997 | Michelson ............. 623/17.16 |
| 5,609,636 A | 3/1997 | Kohrs et al. |
| 5,609,637 A | 3/1997 | Biedermann et al. |
| 5,616,144 A | 4/1997 | Yapp et al. |
| 5,676,699 A | 10/1997 | Gogolewski et al. |
| 5,683,394 A | 11/1997 | Rinner |
| 5,683,463 A | 11/1997 | Godefroy |
| 5,702,449 A | 12/1997 | McKay |
| 5,702,451 A | 12/1997 | Biedermann et al. |
| 5,702,453 A | 12/1997 | Rabbe et al. |
| 5,702,455 A | 12/1997 | Saggar |
| 5,713,899 A | 2/1998 | Marnay et al. |
| 5,728,159 A | 3/1998 | Stroever et al. |
| 5,735,905 A | 4/1998 | Parr |
| 5,755,796 A | 5/1998 | Ibo et al. |
| 5,766,253 A | 6/1998 | Brosnahan, III |
| 5,776,194 A | 7/1998 | Mikol et al. |
| 5,776,196 A | 7/1998 | Matsuzaki et al. |
| 5,776,197 A | 7/1998 | Rabbe et al. |
| 5,776,198 A | 7/1998 | Rabbe et al. |
| 5,776,199 A | 7/1998 | Michelson |
| 5,782,915 A | 7/1998 | Stone |
| 5,785,710 A | 7/1998 | Michelson |
| 5,800,433 A | 9/1998 | Benzel et al. |
| 5,861,041 A | 1/1999 | Tienboon |
| 5,865,845 A | 2/1999 | Thalgott |
| 5,865,849 A | 2/1999 | Stone |
| 5,876,402 A | 3/1999 | Errico et al. |
| 5,876,452 A | 3/1999 | Athanasiou et al. |
| 5,885,299 A | 3/1999 | Winslow et al. |
| 5,888,222 A | 3/1999 | Coates et al. |
| 5,888,223 A | 3/1999 | Bray, Jr. |
| 5,888,224 A | 3/1999 | Beckers et al. |
| 5,888,227 A | 3/1999 | Cottle |
| 5,895,426 A | 4/1999 | Scarborough et al. |
| 5,899,939 A | 5/1999 | Boyce et al. |
| 5,902,338 A | 5/1999 | Stone |
| 5,904,719 A | 5/1999 | Errico et al. |
| 5,910,315 A | 6/1999 | Stevenson et al. |
| 5,922,027 A | 7/1999 | Stone |
| 5,944,755 A | 8/1999 | Stone |
| 5,954,722 A | 9/1999 | Bono |
| 5,968,098 A | 10/1999 | Winslow |
| 5,972,368 A | 10/1999 | McKay |
| 5,976,187 A | 11/1999 | Richelsoph |
| 5,980,522 A | 11/1999 | Koros et al. |
| 5,981,828 A | 11/1999 | Nelson et al. |
| 5,984,967 A | 11/1999 | Zdeblick et al. |
| 5,989,289 A | 11/1999 | Coates et al. |
| 6,013,853 A | 1/2000 | Athanasiou et al. |
| 6,025,538 A | 2/2000 | Yaccarino, III |
| 6,033,405 A | 3/2000 | Winslow et al. |
| 6,033,438 A | 3/2000 | Bianchi et al. |
| 6,039,762 A | 3/2000 | McKay |
| 6,045,579 A | 4/2000 | Hochshuler et al. |
| 6,045,580 A | 4/2000 | Scarborough et al. |
| 6,056,749 A | 5/2000 | Kuslich |
| 6,066,175 A * | 5/2000 | Henderson et al. ........ 623/17.11 |
| 6,080,158 A | 6/2000 | Lin |
| 6,080,193 A | 6/2000 | Hochshuler et al. |
| 6,090,998 A | 7/2000 | Grooms et al. |
| 6,096,080 A | 8/2000 | Nicholson et al. |
| 6,096,081 A | 8/2000 | Grivas et al. |
| 6,099,531 A | 8/2000 | Bonutti |
| 6,110,482 A | 8/2000 | Khouri et al. |
| 6,113,638 A * | 9/2000 | Williams et al. ............... 128/898 |
| 6,120,503 A | 9/2000 | Michelson |
| 6,123,731 A | 9/2000 | Boyce et al. |
| 6,129,763 A | 10/2000 | Chauvin et al. |
| 6,136,001 A | 10/2000 | Michelson |
| 6,139,550 A | 10/2000 | Michelson |
| 6,143,030 A | 11/2000 | Schroder |
| 6,143,033 A | 11/2000 | Paul et al. |
| 6,156,070 A | 12/2000 | Incavo et al. |
| 6,193,721 B1 | 2/2001 | Michelson |
| 6,193,756 B1 | 2/2001 | Studer et al. |
| 6,200,347 B1 | 3/2001 | Anderson et al. |
| 6,206,922 B1 | 3/2001 | Zdeblick et al. |
| 6,224,602 B1 * | 5/2001 | Hayes ............. 606/296 |
| 6,231,610 B1 | 5/2001 | Geisler |
| 6,235,033 B1 | 5/2001 | Brace et al. |
| 6,235,034 B1 | 5/2001 | Bray |
| 6,235,059 B1 | 5/2001 | Benezech et al. |
| 6,241,769 B1 | 6/2001 | Nicholson et al. |
| 6,245,108 B1 | 6/2001 | Biscup |
| 6,258,089 B1 | 7/2001 | Campbell et al. |
| 6,258,125 B1 | 7/2001 | Paul et al. |
| 6,261,291 B1 | 7/2001 | Talaber et al. |
| 6,261,586 B1 | 7/2001 | McKay |
| 6,264,695 B1 | 7/2001 | Stoy |
| 6,270,528 B1 | 8/2001 | McKay |
| 6,306,139 B1 | 10/2001 | Fuentes |
| 6,322,562 B1 | 11/2001 | Wolter |
| 6,342,074 B1 | 1/2002 | Simpson |
| 6,364,880 B1 | 4/2002 | Michelson |
| 6,371,986 B1 | 4/2002 | Bagby |
| 6,383,186 B1 | 5/2002 | Michelson |
| 6,387,130 B1 | 5/2002 | Stone et al. |
| 6,413,259 B1 * | 7/2002 | Lyons et al. ............. 606/295 |
| 6,423,063 B1 | 7/2002 | Bonutti |
| 6,432,106 B1 * | 8/2002 | Fraser ............. 623/17.11 |
| 6,447,512 B1 | 9/2002 | Landry et al. |
| 6,447,546 B1 | 9/2002 | Bramlet et al. |

(56) References Cited

U.S. PATENT DOCUMENTS

| | | |
|---|---|---|
| 6,454,771 B1 | 9/2002 | Michelson |
| 6,458,158 B1 | 10/2002 | Anderson et al. |
| 6,468,311 B2 | 10/2002 | Boyd et al. |
| 6,471,724 B2 | 10/2002 | Zdeblick et al. |
| 6,503,250 B2 | 1/2003 | Paul |
| 6,524,312 B2 | 2/2003 | Landry et al. |
| 6,558,387 B2 | 5/2003 | Errico et al. |
| 6,558,423 B1 * | 5/2003 | Michelson .............. 623/17.11 |
| 6,562,073 B2 | 5/2003 | Foley |
| 6,569,201 B2 | 5/2003 | Moumene et al. |
| 6,575,975 B2 | 6/2003 | Brace et al. |
| 6,576,017 B2 | 6/2003 | Foley et al. |
| 6,605,090 B1 | 8/2003 | Trieu et al. |
| 6,616,671 B2 | 9/2003 | Landry et al. |
| 6,620,163 B1 | 9/2003 | Michelson |
| 6,623,486 B1 | 9/2003 | Weaver et al. |
| 6,629,998 B1 | 10/2003 | Lin |
| 6,638,310 B2 | 10/2003 | Lin et al. |
| 6,645,212 B2 | 11/2003 | Goldhahn et al. |
| 6,656,181 B2 | 12/2003 | Dixon et al. |
| 6,679,887 B2 | 1/2004 | Nicholson et al. |
| 6,682,563 B2 | 1/2004 | Scharf |
| 6,695,846 B2 | 2/2004 | Richelsoph et al. |
| 6,695,851 B2 | 2/2004 | Zdeblick et al. |
| 6,709,456 B2 | 3/2004 | Langberg et al. |
| 6,712,818 B1 | 3/2004 | Michelson |
| 6,730,127 B2 | 5/2004 | Michelson |
| 6,736,850 B2 | 5/2004 | Davis |
| 6,761,739 B2 | 7/2004 | Shepard |
| 6,786,909 B1 * | 9/2004 | Dransfeld et al. ............ 606/283 |
| 6,805,714 B2 | 10/2004 | Sutcliffe |
| 6,808,537 B2 | 10/2004 | Michelson |
| 6,824,564 B2 | 11/2004 | Crozet |
| 6,837,905 B1 | 1/2005 | Lieberman |
| 6,849,093 B2 | 2/2005 | Michelson |
| 6,855,168 B2 | 2/2005 | Crozet |
| 6,884,242 B2 | 4/2005 | LeHuec et al. |
| 6,890,334 B2 | 5/2005 | Brace et al. |
| 6,899,735 B2 | 5/2005 | Coates et al. |
| 6,916,320 B2 | 7/2005 | Michelson |
| 6,962,606 B2 | 11/2005 | Michelson |
| 6,972,019 B2 | 12/2005 | Michelson |
| 6,972,035 B2 | 12/2005 | Michelson |
| 6,974,479 B2 | 12/2005 | Trieu |
| 6,984,234 B2 | 1/2006 | Bray |
| 7,001,385 B2 | 2/2006 | Bonutti |
| 7,001,432 B2 | 2/2006 | Keller et al. |
| 7,033,394 B2 | 4/2006 | Michelson |
| 7,041,135 B2 | 5/2006 | Michelson |
| 7,044,968 B1 | 5/2006 | Yaccarino, III et al. |
| 7,060,097 B2 | 6/2006 | Fraser et al. |
| 7,077,864 B2 | 7/2006 | Byrd, III et al. |
| 7,112,222 B2 | 9/2006 | Fraser et al. |
| 7,112,223 B2 | 9/2006 | Davis |
| 7,135,024 B2 | 11/2006 | Cook et al. |
| 7,135,043 B2 | 11/2006 | Nakahara et al. |
| 7,137,984 B2 | 11/2006 | Michelson |
| 7,147,665 B1 | 12/2006 | Bryan et al. |
| 7,163,561 B2 | 1/2007 | Michelson |
| 7,172,627 B2 | 2/2007 | Fiere et al. |
| 7,172,672 B2 | 2/2007 | Silverbrook |
| 7,232,463 B2 | 6/2007 | Falahee |
| 7,232,464 B2 | 6/2007 | Mathieu et al. |
| 7,255,698 B2 | 8/2007 | Michelson |
| 7,276,082 B2 | 10/2007 | Zdeblick et al. |
| 7,320,708 B1 | 1/2008 | Bernstein |
| 7,323,011 B2 | 1/2008 | Shepard et al. |
| 7,608,107 B2 | 10/2009 | Michelson |
| 7,618,456 B2 | 11/2009 | Mathieu et al. |
| 7,826,207 B2 | 11/2010 | Wang |
| 7,862,616 B2 | 1/2011 | Lechmann et al. |
| 7,875,076 B2 | 1/2011 | Mathieu et al. |
| 8,328,872 B2 | 12/2012 | Duffield et al. |
| 8,343,222 B2 | 1/2013 | Cope |
| 2001/0001129 A1 | 5/2001 | McKay et al. |
| 2001/0005796 A1 | 6/2001 | Zdeblick et al. |
| 2001/0010021 A1 | 7/2001 | Boyd et al. |
| 2001/0016777 A1 | 8/2001 | Biscup |
| 2001/0031254 A1 | 10/2001 | Bianchi et al. |
| 2001/0039456 A1 | 11/2001 | Boyer, II et al. |
| 2001/0041941 A1 | 11/2001 | Boyer et al. |
| 2002/0004683 A1 | 1/2002 | Michelson et al. |
| 2002/0010511 A1 | 1/2002 | Michelson |
| 2002/0016595 A1 | 2/2002 | Michelson |
| 2002/0022843 A1 | 2/2002 | Michelson |
| 2002/0029084 A1 | 3/2002 | Paul et al. |
| 2002/0065517 A1 * | 5/2002 | Paul ................... 606/69 |
| 2002/0082597 A1 | 6/2002 | Fraser |
| 2002/0082603 A1 | 6/2002 | Dixon et al. |
| 2002/0091447 A1 | 7/2002 | Shimp et al. |
| 2002/0099376 A1 | 7/2002 | Michelson |
| 2002/0995155 | 7/2002 | Michelson |
| 2002/0106393 A1 | 8/2002 | Bianchi et al. |
| 2002/0111680 A1 | 8/2002 | Michelson |
| 2002/0128712 A1 | 9/2002 | Michelson |
| 2002/0128717 A1 | 9/2002 | Alfaro et al. |
| 2002/0147450 A1 * | 10/2002 | LeHuec et al. ................. 606/61 |
| 2002/0169508 A1 | 11/2002 | Songer et al. |
| 2002/0193880 A1 | 12/2002 | Fraser |
| 2003/0078666 A1 | 4/2003 | Ralph et al. |
| 2003/0078668 A1 | 4/2003 | Michelson |
| 2003/0125739 A1 | 7/2003 | Bagga et al. |
| 2003/0135277 A1 | 7/2003 | Bryan et al. |
| 2003/0153975 A1 | 8/2003 | Byrd et al. |
| 2003/0167092 A1 | 9/2003 | Foley |
| 2003/0195626 A1 | 10/2003 | Huppert |
| 2003/0195632 A1 | 10/2003 | Foley et al. |
| 2004/0078078 A1 * | 4/2004 | Shepard .................... 623/17.11 |
| 2004/0078081 A1 | 4/2004 | Ferree |
| 2004/0093084 A1 | 5/2004 | Michelson |
| 2004/0102848 A1 | 5/2004 | Michelson |
| 2004/0126407 A1 * | 7/2004 | Falahee ........................ 424/423 |
| 2004/0176853 A1 | 9/2004 | Sennett et al. |
| 2004/0199254 A1 | 10/2004 | Louis et al. |
| 2004/0210310 A1 | 10/2004 | Trieu |
| 2004/0210314 A1 | 10/2004 | Michelson |
| 2004/0249377 A1 | 12/2004 | Kaes et al. |
| 2004/0254644 A1 | 12/2004 | Taylor |
| 2005/0015149 A1 | 1/2005 | Michelson |
| 2005/0021143 A1 | 1/2005 | Keller |
| 2005/0033433 A1 | 2/2005 | Michelson |
| 2005/0049593 A1 | 3/2005 | Duong et al. |
| 2005/0049595 A1 | 3/2005 | Suh et al. |
| 2005/0065608 A1 | 3/2005 | Michelson |
| 2005/0071008 A1 | 3/2005 | Kirschman |
| 2005/0085913 A1 | 4/2005 | Fraser et al. |
| 2005/0101960 A1 | 5/2005 | Fiere et al. |
| 2005/0159813 A1 | 7/2005 | Molz |
| 2005/0159819 A1 | 7/2005 | McCormack et al. |
| 2005/0240271 A1 | 10/2005 | Zubok et al. |
| 2006/0030851 A1 | 2/2006 | Bray et al. |
| 2006/0079901 A1 | 4/2006 | Ryan et al. |
| 2006/0079961 A1 | 4/2006 | Michelson |
| 2006/0085071 A1 | 4/2006 | Lechmann et al. |
| 2006/0129240 A1 | 6/2006 | Lessar et al. |
| 2006/0136063 A1 | 6/2006 | Zeegers |
| 2006/0142765 A9 | 6/2006 | Dixon et al. |
| 2006/0195189 A1 | 8/2006 | Link et al. |
| 2006/0206208 A1 | 9/2006 | Michelson |
| 2007/0088441 A1 | 4/2007 | Duggal et al. |
| 2007/0118125 A1 | 5/2007 | Orbay et al. |
| 2007/0123987 A1 | 5/2007 | Bernstein |
| 2007/0162130 A1 | 7/2007 | Rashbaum et al. |
| 2007/0168032 A1 | 7/2007 | Muhanna et al. |
| 2007/0177307 A1 | 8/2007 | Fujimoto |
| 2007/0219635 A1 | 9/2007 | Mathieu et al. |
| 2007/0225806 A1 | 9/2007 | Squires et al. |
| 2007/0225812 A1 | 9/2007 | Gill |
| 2007/0270961 A1 | 11/2007 | Ferguson |
| 2008/0051890 A1 | 2/2008 | Waugh et al. |
| 2008/0119933 A1 | 5/2008 | Aebi et al. |
| 2008/0133013 A1 | 6/2008 | Duggal et al. |
| 2008/0249569 A1 | 10/2008 | Waugh et al. |
| 2008/0249575 A1 | 10/2008 | Waugh et al. |

(56) References Cited

U.S. PATENT DOCUMENTS

| | | |
|---|---|---|
| 2008/0269806 A1 | 10/2008 | Zhang et al. |
| 2008/0306596 A1 | 12/2008 | Jones et al. |
| 2009/0076608 A1 | 3/2009 | Gordon et al. |
| 2009/0105830 A1 | 4/2009 | Jones et al. |
| 2009/0210064 A1 | 8/2009 | Lechmann et al. |
| 2010/0016901 A1 | 1/2010 | Robinson |

FOREIGN PATENT DOCUMENTS

| | | |
|---|---|---|
| DE | 3933459 | 4/1991 |
| DE | 4242889 | 6/1994 |
| DE | 4409392 | 9/1995 |
| DE | 4423257 | 1/1996 |
| DE | 19504867 | 2/1996 |
| DE | 29913200 | 9/1999 |
| EP | 0505634 A1 | 9/1992 |
| EP | 0517030 | 12/1992 |
| EP | 0517030 A3 | 4/1993 |
| EP | 0577178 | 1/1994 |
| EP | 0639351 | 3/1995 |
| EP | 0517030 B1 | 9/1996 |
| EP | 0505634 B1 | 8/1997 |
| EP | 0906065 | 4/1999 |
| EP | 0966930 | 4/1999 |
| EP | 0968692 | 1/2000 |
| EP | 0974319 A2 | 1/2000 |
| EP | 1033941 | 9/2000 |
| EP | 1051133 | 11/2000 |
| EP | 1103236 | 5/2001 |
| FR | 2552659 | 4/1985 |
| FR | 2700947 | 8/1985 |
| FR | 2697996 | 5/1994 |
| FR | 2727003 | 5/1996 |
| FR | 2747034 | 10/1997 |
| FR | 2753368 | 3/1998 |
| GB | 2148122 | 5/1985 |
| GB | 2207607 | 2/1989 |
| SU | 1465040 | 3/1989 |
| WO | WO 88/03417 | 5/1988 |
| WO | WO 88/10100 | 12/1988 |
| WO | WO 92/01428 | 2/1992 |
| WO | WO 95/21053 | 8/1995 |
| WO | WO 99/29271 | 6/1996 |
| WO | WO 96/39988 | 12/1996 |
| WO | WO 97/20526 | 6/1997 |
| WO | WO 97/25941 | 7/1997 |
| WO | WO 97/25945 | 7/1997 |
| WO | WO 97/39693 | 10/1997 |
| WO | WO 98/17209 | 4/1998 |
| WO | WO 98/55052 | 12/1998 |
| WO | WO 98/56319 | 12/1998 |
| WO | WO 98/56433 | 12/1998 |
| WO | WO 99/27864 | 6/1999 |
| WO | WO 99/32055 | 7/1999 |
| WO | WO 99/38461 | 8/1999 |
| WO | WO 99/38463 | 8/1999 |
| WO | WO 99/56675 | 11/1999 |
| WO | WO 99/63914 | 12/1999 |
| WO | WO 00/07527 | 2/2000 |
| WO | WO 00/07528 | 2/2000 |
| WO | WO 00/30568 | 6/2000 |
| WO | WO 00/40177 | 7/2000 |
| WO | WO 00/41654 | 7/2000 |
| WO | WO 00/59412 | 10/2000 |
| WO | WO 00/66044 | 11/2000 |
| WO | WO 00/66045 | 11/2000 |
| WO | WO 00/74607 | 12/2000 |
| WO | WO 01/08611 | 2/2001 |
| WO | WO 01/56497 B1 | 8/2001 |
| WO | WO 01/62190 | 8/2001 |
| WO | WO 01/80785 | 11/2001 |
| WO | WO 01/56497 A3 | 12/2001 |
| WO | WO 01/93742 A2 | 12/2001 |
| WO | WO 01/95837 | 12/2001 |
| WO | WO 01/93742 A3 | 9/2002 |
| WO | WO 2004/069106 | 8/2004 |
| WO | WO 2007/098288 | 8/2007 |
| WO | WO 2009/064644 | 5/2009 |

OTHER PUBLICATIONS

U.S. Appl. No. 11/199,599: Amendment/Request for Reconsideration after Non-Final Rejection, dated Sep. 29, 2009, 30 pages.

U.S. Appl. No. 11/199,599: Appeal Brief, dated Apr. 15, 2010, 51 pages.

U.S. Appl. No. 11/199,599: Final Rejection, dated Dec. 24, 2009, 21 pages.

U.S. Appl. No. 11/199,599: Interview Summary included Draft Amendments, dated Sep. 24, 2009, 16 pages.

U.S. Appl. No. 11/199,599: Non-Final Rejection, dated Apr. 1, 2009, 20 pages.

U.S. Appl. No. 11/199,599: Preliminary Amendment, dated Jan. 9, 2008, 11 pages.

"Jury Trial Demanded", In the United States District Court for the District of Delaware, Case No. 1:11-cv-00652-LPS, filed Jul. 22, 2011, 8 pages.

Chadwick et al., "Radiolucent Structural Materials for Medical Applications," www.mddionline.com/print/238, Jun. 1, 2001, accsessed date Jul. 31, 2012, 9 pages.

Jonbergen et al., "Anterior Cervical Interbody fusion with a titanium box cage: Early radiological assessment of fusion and subsidence", The Spine Journal 5, Jul. 2005, 645-649.

Marcolongo et al., "Trends in Materials for Spine Surgery", Biomaterials and Clinical Use, 6, 2011, 21 pages.

Parlov et al., Anterior Lumbar Interbody Fusion with Threaded Fusion Cages and Autologous Grafts, Eur. Spine J., 2000, 9, 224-229.

Schleicher et al., "Biomechanical Comparison of Two Different Concepts for Stand alone anterior lumbar interbody fusion", Eur. Spine J., Sep. 2008, 17, 1757-1765.

Scholz et al., "A New Stand-Alone Cervical Anterior Interbody Fusion Device", Spine, Jan. 2009, 34(2), 6 pages.

Spruit et al., The in Vitro Stabilising Effect of Polyether-etherketone Cages Versus a Titanium Cage of similar design for anterior lumbar interbody fusion, Eur. Spine J., Aug. 2005, 14 752-758.

"Expert Report of Paul Ducheyne, Ph.D. Concerning Patent Validity", United States District Court District of Delaware, Civil Action No. 1:11-cv-00652-LPS, Dec. 13, 2012, 155 pages.

"Expert Report of Richard J. Gering, Ph.D., CLP" In the United States District Court for the District of Delaware, Civil Action No. 1:11-cv-00652-LPS, Dec. 14, 2012, 39 pages.

"Expert Report of John F. Hall, M.D.", United States District Court for the District of Delaware, Civil Action No. 1:11-cv-00652-LPS, Dec. 14, 2012, 27 pages.

"Second Expert Report of Wilson C. Hayes, Ph.D.", United States District Court for the District of Delaware, Civil Action No. 1:11-cv-00652-LPS, Dec. 14, 2012, 22 pages.

"Expert Report of Dr. Domagoj Coric Regarding the Invalidity of U.S. Patent Nos. 7,846,207, 7,862,616 and 7,875,076", In the United States District Court for the District of Delaware, Civil Action No. 1:11-cv-00652-LPS, Nov. 5, 2012, 149 pages.

"Reply Report of Dr. Domagoj Coric Regarding the Invalidity of U.S. Patent Nos. 7,846,207, 7,862,616 and 7,875,076", In the United States District Court for the District of Delaware, Civil Action No. 1:11-cv-00652-LPS, Jan. 4, 2013, 81 pages.

"Joint Claim Construction Brief", In the United States District Court for the District of Delaware, Civil Action No. 1:11-cv-00652-LPS, Jun. 14, 2012, 97 pages.

"Plaintiffs' Responses and Objections to Defendant Globus Medical, Inc.'s First Set of Interrogatories (Nos. 1-11)", United States District Court for the District of Delaware, Civil Action No. 1:11-cv-00652-LPS, Nov. 14, 2011, 18 pages.

"Plaintiffs' Supplemental Responses and Objections to Defendant Globus Medical Inc.'s Interrogatories Nos. 6-10 and Second Supplemental Responses and Objections to Interrogatory No. 5", United States District Court for the District of Delaware, Civil Action No. 11-cv-652-LPS, Sep. 1, 2012, 12 pages.

(56) References Cited

OTHER PUBLICATIONS

"Appendix 1 to Joint Claim Construction Brief; Synthes' Exhibits A-9", In the United States District Court for the District of Delaware Civil Action No. 1:11-cv-00652-LPS, Jun. 8, 2012, 192 pages.
"Appendix 2 to Joint Claim Construction Brief; Globus' Exhibits A-F", In the United States District Court for the District of Delaware Civil Action No. 1:11-cv-00652-LPS, Jun. 8, 2012, 146 pages.
"Appendix 3 to Joint Claim Construction Brief; Exhibits A-C", In the United States District Court for the District of Delaware Civil Action No. 1:11-cv-00652-LPS, Jun. 8, 2012, 38 pages.
Trial Transcript, United States District Court District of Delaware, Civil Action No. 1:11-cv-00652-LPS, Jun. 3, 2013, 98 pages.
Trial Transcript, United States District Court District of Delaware, Civil Action No. 1:11-cv-00652-LPS, Jun. 4, 2013, 110 pages.
Trial Transcript, United States District Court District of Delaware, Civil Action No. 1:11-cv-00652-LPS, Jun. 5, 2013, 99 pages.
Trial Transcript, United States District Court District of Delaware, Civil Action No. 1:11-cv-00652-LPS, Jun. 6, 2013, 80 pages.
Trial Transcript, United States District Court District of Delaware, Civil Action No. 1:11-cv-00652-LPS, Jun. 7, 2013, 97 pages.
Trial Transcript, United States District Court District of Delaware, Civil Action No. 1:11-cv-00652-LPS, Jun. 10, 2013, 114 pages.
Trial Transcript, United States District Court District of Delaware, Civil Action No. 1:11-cv-00652-LPS, Jun. 11, 2013, 98 pages.
Trial Transcript, United States District Court District of Delaware, Civil Action No. 1:11-cv-00652-LPS, Jun. 12, 2013, 75 pages.
Trial Transcript, United States District Court District of Delaware, Civil Action No. 1:11-cv-00652-LPS, Jun. 13, 2013, 94 pages.
Trial Transcript, United States District Court District of Delaware, Civil Action No. 1:11-cv-00652-LPS, Jun. 14, 2013, 26 pages.
Jury Verdict Form, United States District Court District of Delaware, Civil Action No. 1:11-cv-00652-LPS, Jun. 14, 2013, 20 pages.
"Memorandum Opinion" United States District Court District of Delaware, Civil Action No. 1:11-cv-00652-LPS, May 7, 2013, 33 pages.
"Order" United States District Court District of Delaware, Civil Action No. 1:11-cv-00652-LPS, May 7, 2013, 7 pages.
Redacted version of "Opening Brief in Support of Plaintiffs' Motion for Summary Judgment of No Anticipation by the Kozak and Michelson References", United States District Court District of Delaware, Civil Action No. 1:11-cv-00652-LPS, Feb. 13, 2013, 66 pages.
Redacted version of "Defendant Globus Medical, Inc.'s Answering Brief in Opposition to Plaintiff's Motion for Summary Judgment of No Anticipation by the Kozak and Michelson References", Mar. 12, 2013, 233 pages.
Redacted version of "Plaintiff's Reply Brief in Support of Plaintiff's Motion for Summary Judgment of No Anticipation by the Kozak and Michelson References", Mar. 21, 2013, 11 pages.
"Order" United States District Court District of Delaware, Civil Action No. 1:11-cv-00652-LPS, May 15, 2013, 4 pages.

* cited by examiner

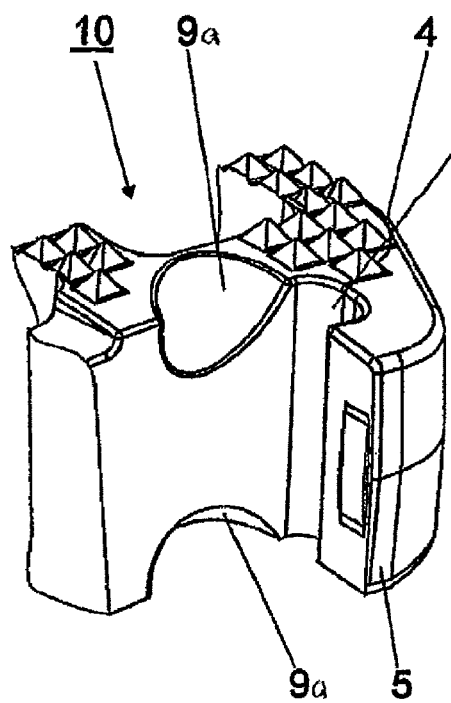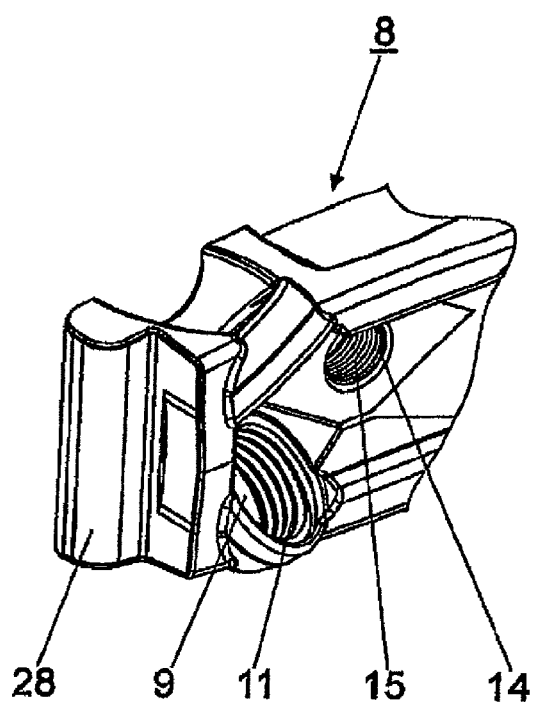
Fig. 5
Fig. 6

INTERVERTEBRAL IMPLANT

CROSS REFERENCE TO RELATED APPLICATION

This application is a continuation of U.S. patent application Ser. No. 12/969,330, filed Dec. 15, 2010, which is a continuation of U.S. patent application Ser. No. 12/432,088, filed Apr. 29, 2009, now U.S. Pat. No. 7,862,616, which is a continuation of U.S. patent application Ser. No. 11/199,599, filed Aug. 8, 2005, now U.S. Pat. No. 7,846,207, which is a continuation of International Patent Application No. PCT/CH2003/000089, filed Feb. 6, 2003. The disclosure of each of the above-identified patent applications is incorporated by reference as if set forth in its entirety herein.

TECHNICAL FIELD

The present invention relates generally to intervertebral implants.

BACKGROUND

GB-A-2 207 607 discloses an intervertebral implant, which has a horseshoe shaped configuration with a plurality of cylindrical holes. The holes are smooth on the inside and only have a stop for the heads of the bone screws, which are to be introduced therein. A disadvantage of this arrangement is that the fastening screws, introduced therein, can be anchored only with their shaft in the bone. This does not result in a rigid connection with the horseshoe-shaped intervertebral implant. When the anchoring of the screw shaft in the bone is weakened, the intervertebral implant becomes movable with respect to the screw and the bone screws tend to migrate, endangering the blood vessels. Moreover, the loosening of the intervertebral implant can lead to a pseudoarthrosis.

U.S. Patent Publication US-A 2000/0010511 (Michelson) discloses an intervertebral implant, which, at its front surface, has two boreholes with an internal thread, into which bone screws with a threaded head can be introduced. A disadvantage of this implant is that the bone screws can become loose and are not secured against being screwed out or falling out. A further disadvantage is that the bone screws are fastened completely to the implant body itself and that therefore the latter experiences a relatively large stress.

Screws which emerge at the anterior or anterolateral edge of the vertebral body because of loosening run the risk of injuring main vessels such as the aorta and Vena calva, as well as supply vessels such as lumbar arteries and veins. Injury to these main vessels may result in internal bleeding possibly causing death within a very short time. Loosening of screws is more likely when they are not mounted angularly firmly.

SUMMARY

The present invention is to provide a remedy for the above-discussed disadvantages. The present invention is directed to an intervertebral implant which can enter into a permanent, rigid connection with bone fixation means, so that, even if the bone structure is weakened, there is no loosening between the intervertebral implant and the bone fixation means. Moreover, over a separately constructed front plate, there is tension chording for the bone fixation elements, so that the implant body experiences less stress, that is, superimposed tensions. Moreover, a securing plate enables all bone fixation elements to be secured simultaneously.

The present invention accomplishes the objective set out above with an intervertebral implant, comprising a three-dimensional body having an upper side and an under side which are suitable for abutting the end plates of two adjacent vertebral bodies. The three-dimensional body further includes a left side surface and a right side surface, a front surface and a rear surface, a horizontal middle plane between the upper side and the under side, and a vertical middle plane extending from the front surface to the tear surface. The three-dimensional body further comprising a plurality of boreholes, having openings at least at or near the front surface, passing there through and being suitable for accommodating longitudinal fixation elements. The intervertebral implant further including a front plate displaceably disposed as an insert with the front side of the three-dimensional body, where the front plate includes a plurality of boreholes having openings and in which the longitudinal fixation elements can be anchored, and whose openings overlap with the openings of the boreholes of the three-dimensional body. The intervertebral implant has a securing plate fastened substantially parallel to the front plate in such a manner that the boreholes of the front plate are covered at least partly by the securing plate. An advantage achieved by the present invention, arises essentially from the solid connection between the intervertebral implant and the longitudinal fixation elements, used to fasten it.

Compared to the two-part implants of the state of the art, for which a front plate is implanted in a separate step, the present invention has the advantage that the implantation of the intervertebral implant may be carried out in one step and, with that, can be carried out more easily and more quickly. A further advantage is that the intervertebral implant is fixed as frontally as possible at the body of the vertebra. That is, at a place where good bone material usually is present. The result is an anterior movement limitation without a greater risk to the surrounding structures. The load is still absorbed under compression by the intervertebral implant and not by the front plate or the fixation screws (longitudinal fixation elements).

A method for implanting an intervertebral implant of the present invention between two adjacent vertebral bodies includes introducing the intervertebral implant, having a three-dimensional body, a front plate, and one or more boreholes, between two adjacent vertebral bodies, attaching longitudinal fixation elements with heads through the boreholes into the vertebral bodies, and attaching a securing plate by means of a fastening agent over the heads of the longitudinal fixation elements to the front plate, such that the heads of the longitudinal fixation elements are captured between the front plate and the securing plate wherein the longitudinal fixation elements are secured against being shifted relative to the intervertebral implant.

Other objectives and advantages in addition to those discussed above will become apparent to those skilled in the art during the course of the description of a preferred embodiment of the invention which follows. In the description, reference is made to accompanying drawings, which form a part thereof, and which illustrate an example of the invention. Such example, however, is not exhaustive of the various embodiments of the invention, and therefore, reference is made to the claims that follow the description for determining the scope of the invention.

BRIEF DESCRIPTION OF THE DRAWINGS

FIG. 5 shows a three-dimensional detailed representation of the body of the intervertebral implant, which shows the connecting elements to the front plate of FIG. 6, FIG. 6 shows a three-dimensional detailed representation of the front plate of the intervertebral implant and the connecting elements to the body of FIG. 5

DETAILED DESCRIPTION OF ILLUSTRATIVE EMBODIMENTS

Figure 1:
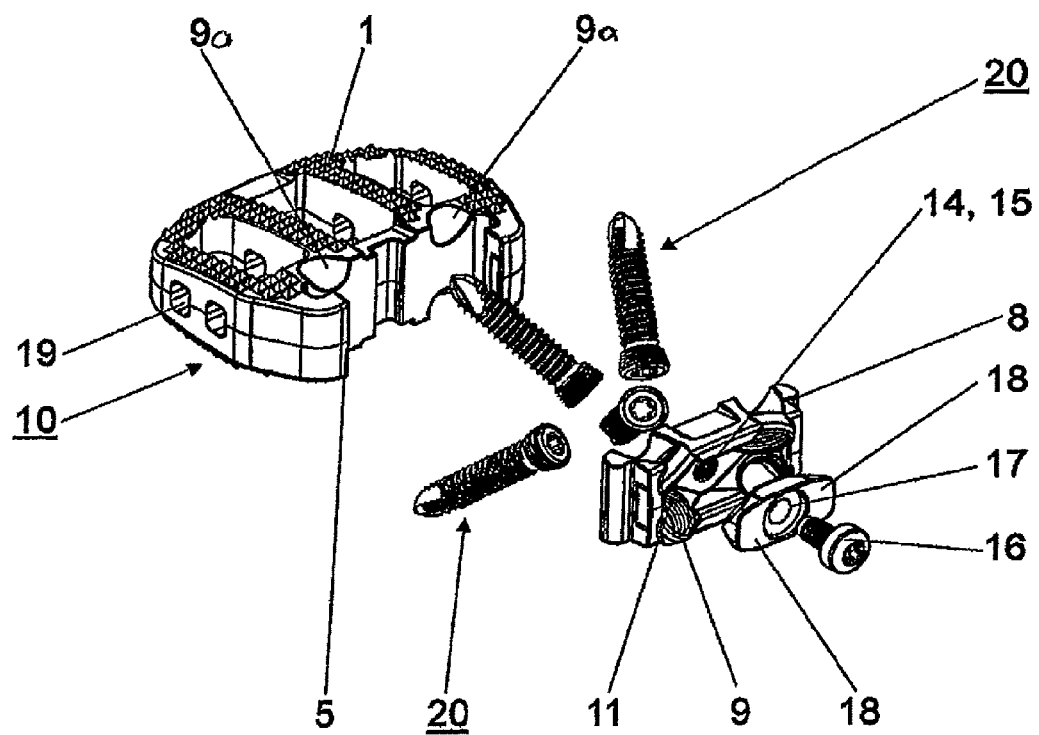
FIG. 1 shows an exploded drawing of the intervertebral implant.

The intervertebral implant, shown in FIGS. 1-7, includes a three-dimensional body 10 in the form of a cage with an upper side 1 and an underside 2, which are suitable for abutting the end plates of two adjacent vertebral bodies, a left side surface 3 and a right side surface 4, a front surface 5 and a back surface 6, a horizontal middle plane 7 located between the upper side 1 and the underside 2, a vertical middle plane 12 extending from the front surface 5 to the rear surface 6 and four boreholes 9a, which pass through the body 10 and are suitable for accommodating longitudinal fixation elements 20. The body 10 may be constructed as a hollow body, the mantle surfaces of which are provided with perforations 19. The upper side 1 and/or under side 2 of the intervertebral implant may preferably be convex in shape, not planar. A convex shape to the upper side 1 and the underside 2 allows for an improved fit with the end plates of the adjacent vertebral bodies by the intervertebral implant. Further, the side surfaces 1-6 of the intervertebral implant may be essentially convex, as well.

Figure 7:
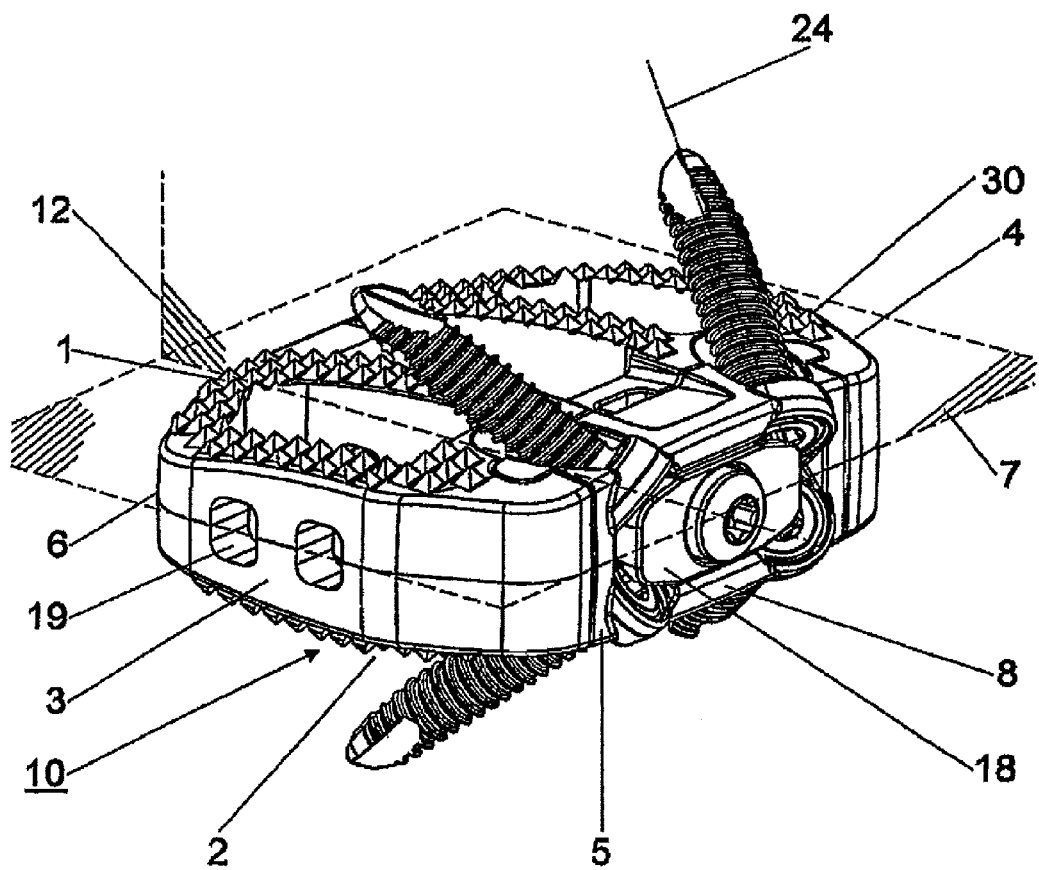
FIG. 7 shows a completely installed intervertebral implant with front plate and securing plate.

As shown in FIG. 7, the upper side 1 and the underside 2 of the three dimensional body 10 are provided with structuring in the form of teeth 30.

At the front surface of the three-dimensional body 10, a front plate 8 may be mounted, which is disposed perpendicular to the horizontal central plane of the intervertebral implant and through which four boreholes 9 pass and in which the longitudinal fixation elements 20 can be anchored. The front plate 8, as shown in FIGS. 5 and 6, is constructed as an insert for the three-dimensional body 10. The three-dimensional body 10 has a semicircular groove 27 extending parallel to the vertical middle plane 12 at the transitions of the left side surface 3 and the right side surface 4 (FIG. 5) to the front surface 5. Correspondingly, the front plate 8 has right and left (FIG. 6) similarly extending and similarly dimensioned, semicircular rail 28. As a result, the front plate can be pushed and positioned easily with its two lateral rails 28 into the corresponding grooves 27 of the body 10 during the production of the intervertebral implant.

In one embodiment, at least one of the boreholes 9 in the front plate is constructed so that a longitudinal fixation element 20, accommodated therein, can be connected rigidly with the front plate. A rigid connection may be accomplished, for example, owing to the fact that at least one of the boreholes 9 of the front plate 8 has an internal thread. A corresponding longitudinal fixation element 20, bone screw, with a threaded end can then be screwed together rigidly with the implant. In an alternative embodiment, the four boreholes 9 in the front plate may have an internal thread 11, so that longitudinal fixation elements 20 can be connected rigidly with the front plate 8.

As discussed, the front plate 8 may be disposed, preferably vertically to the horizontal central plane, so that it can be displaced vertically with respect to the three-dimensional body 10. By these means, "stress shielding" (protection and neutralization of mechanical stresses) is attained, which permits the end plates to be adapted to the intervertebral implant during the healing process.

The intervertebral implant may have a securing plate 18, which can be fastened by means of a screw connection parallel to the front plate 8 at the front plate 8 in such a manner that the boreholes 9 of the front plate 8 are partly covered by the securing plate 18. The securing plate 18 may have a central borehole 17 provided, preferably, with an internal thread. Corresponding thereto, the front plate 8 has a central borehole 15 for accommodating fastening means 16. Preferably, the central borehole 15 has an internal thread 14 for accommodating a fastening means 16 in the form of a screw. The securing plate 18 may also be fastened by a bayonet catch or a click catch. By fastening the securing plate 18 to the front plate 8, the heads 21 of the longitudinal fixation elements 20 (discussed later) are contacted by the securing plate 18, so that they are secured against being ejected or screwed out.

Figure 3:
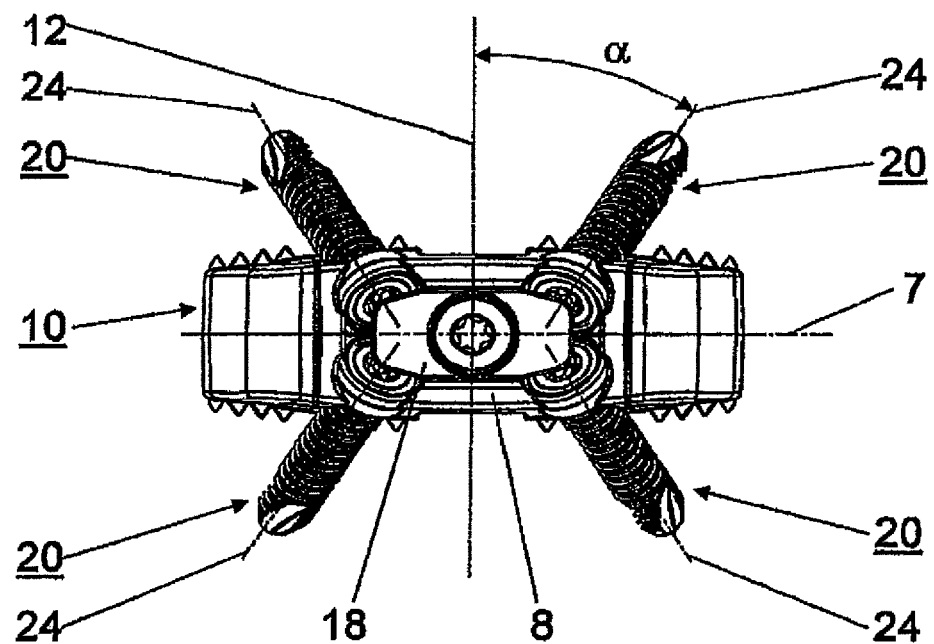
FIG. 3 shows an elevation of the intervertebral implant of FIG. 1.
Figure 4:
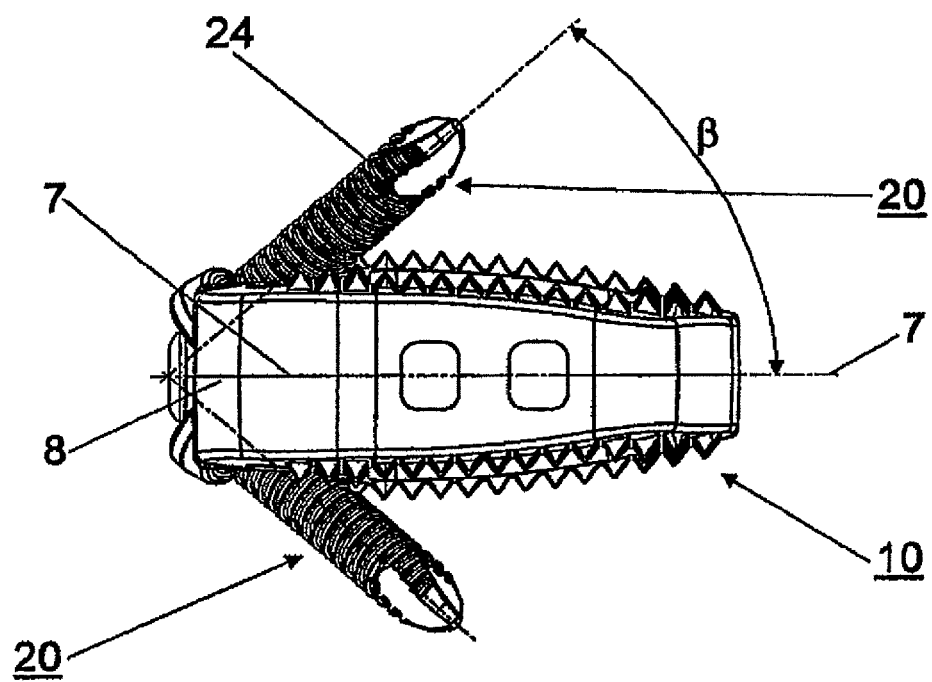
FIG. 4 shows a side view of the intervertebral implant of FIG. 1.

Preferably, the boreholes 9a of the three-dimensional body 10 do not pass either through the left side surface 3 or the right side surface 4 or completely through the front surface 5. The front surface 5, preferably, is also not crossed by the boreholes 9a. Further, the horizontal middle plane 7 is not pierced by the boreholes 9a. Only the axes 24 of the longitudinal fixation elements 20, introduced therein, intersect the horizontal middle plane 7 of the body 10. As seen from the front surface 5, the boreholes of the three-dimensional body 10 and the front plate diverge. The axes 24 of the boreholes of the three-dimensional plate 10 and the front plate 8 enclose an angle ranging from 20° to 60°, specifically from 36° to 48°, and more preferably an angle 13 of 42° with the horizontal middle plane 7 (FIG. 4) and an angle a ranging from 100 to 45°, specifically from 27° to 33°, and more preferably an angle a of 30° with the vertical middle plane 12 (FIG. 3). Thus, better access for introducing the screws is achieved.

In one embodiment, at least one of the boreholes 9 of the front plate 8 may taper conically towards the underside 2, so that a bone screw, with a corresponding conical head, can be anchored rigidly therein. The conical borehole preferably has a conical angle, which is smaller than the resulting frictional angle. Advisably, the conicity of the conical borehole is 1:3.75 to 1:20.00 and preferably 1:5 to 1:15.

To improve the anchoring of the bone screw in a plastic body of the intervertebral implant (discussed later), a metal sleeve with an internal thread (not shown) may be inserted in the boreholes of the front plate and three-dimensional body. The intervertebral implant may also consist only partially of an x-ray transparent plastic and, in the region of the boreholes consist of a metal, such as titanium or a titanium alloy. Improved guidance and anchoring of the bone screws in the intervertebral implant may be achieved. Further, the boreholes 9 may have a smooth internal wall, into which the threaded head of a metallic, longitudinal fixation element may cut or be molded.

Depending on circumstances, two, three, four or more longitudinal fixation elements may be connected rigidly with the intervertebral implant. Preferably, at least one fixation element should pierce the upper side and at least one fixation element the underside of the intervertebral implant. The longitudinal fixation elements 20 may have either a smooth head, so that there will not be a rigid connection with the implant or a threaded, conical or expendable end, so that there will be a rigid connection with the implant. In both cases, however, the longitudinal fixation elements 20 are secured by the securing plate against rotating out, being ejected out or falling out at a later time.

Figure 2:
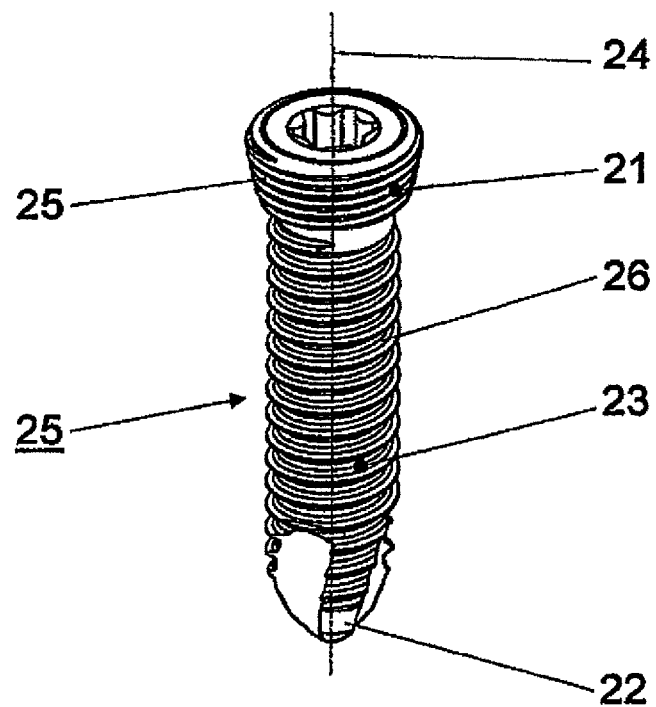
FIG. 2 shows a longitudinal fixation element in the form of a screw.

The longitudinal fixation elements 20 are preferably constructed as bone screws. As shown in FIG. 2, the longitudinal fixation elements 20, introduced into the boreholes 9, have a head 21, a tip 22, a shaft 23 and an axis 24. The head 21 may preferably be provided with an external thread 25, which corresponds to the internal thread 11 of the borehole 9, so that the heads 21 can be anchored in the boreholes 9 in a rigid manner. The shaft 23 may be provided with a thread 26, which is self-drilling and self-cutting. The load thread angle of the thread 26 has a range of between 11° to 14°, preferably between 12° and 13°, and more preferably a load thread angle of 115°. The pitch angle of the thread may have a range of between 6° and 10°, preferably between 7° and 9°, and more preferably have a pitch angle of 8°. The special pitch angle produces a self-retardation in the thread, thus ensuring that the bone screw will not automatically become loose.

In the case of a second, possibly rigid type of connection, a longitudinal fixation element 20, bone screw, may preferably be used, the head of which tapers conically towards the shaft, the conicity of the head corresponding to the conicity of the borehole of the intervertebral implant. The longitudinal fixation elements may also be constructed as threadless cylindrical pins, which are provided with a drilling tip, preferably in the form of a trocar. A further variation consist therein that the longitudinal fixation elements are constructed as spiral springs. Finally, the longitudinal fixation elements may also be constructed as single-vaned or multi-vaned spiral blades.

As shown in FIG. 7, two longitudinal fixation elements 20 pierce the upper side 1 and two longitudinal fixation elements 20 pierce the underside 2 of the body 10, thereby anchoring the intervertebral implant to the adjacent vertebral bodies.

The intervertebral implant may be produced from any material which is compatible with the body. Preferably, the three-dimensional body 10 may consist of a body-compatible plastic which has not been reinforced and which may be transparent to x-rays. The advantage over fiber-reinforced plastics, which are already known in implant technology, is that no reinforcing fibers are exposed. Such exposure may be disadvantageous clinically. In such a three-dimensional body 10 constructed of a plastic that has not been reinforced, the use bone screws may be preferable. As discussed previously, the external thread of the bone screw(s) may have a load thread angle range of 110 to 14°, and preferably between 12° to 130. A comparatively slight inclination of the load flank brings about a high clamping force. As a result, radial expansion and the danger of forming cracks in the plastic are reduced. Furthermore, the external thread of the bone screw(s) may preferably have a pitch angle between 6° and 10° and preferably between 7° and 9°.

The front plate 8 may be made from materials different than the three dimensional body 10. The front plate 8 is preferably made from a metallic material. Titanium or titanium alloys are particularly suitable as metallic materials. The complete tension chord arrangement (front plate and screws) may also be made from implant steel or highly alloyed metallic materials, such as CoCrMo or CoCrMoC. The advantage of titanium lies in that there is good tissue compatibility and the good ingrowing behavior of bones. The advantage of highly alloyed metallic materials lies in their high-strength values, which permit filigree constructions.

A brief description of a surgical procedure follows in order to explain the invention further.

The intervertebral implant, in the form of a three-dimensional body 10, is introduced between two adjacent vertebral bodies by means of a suitable instrument. Longitudinal fixation elements 20, in the form of bone screws, securing the three-dimensional body 10 are screwed/inserted by means of a suitable aiming device through the boreholes 9 of the front plate 8 into the vertebral bodies. The front plate 8 may be displaced vertically with respect to the three-dimensional body 10, such that the openings of the boreholes 9a of the three-dimensional plate 10 and the boreholes 9 of the front plate 8 overlap, to obtain stress shielding. The securing plate 18 is fastened by means of the fastening agent 16 in the form of a screw over the heads 21 of the longitudinal fixation elements 20 at the front plate 8, so that the heads 21 of the longitudinal fixation elements 20 and, with that, the screws themselves, are captured between the front plate 8 and the securing plate 18 and secured against being shifted relative to the three-dimensional body 10 (for example, by falling out or by turning out). The fastening agent 16, in the form of a screw, preferably is provided with a thread, which is distinguished by a large self-retardation.

What is claimed:

1. An intervertebral implant configured to be inserted into an intervertebral space, the intervertebral implant comprising:
   (a) a one-piece body defining a front body surface, a rear body surface opposite the front body surface, an upper body surface, a lower body surface spaced from the upper body surface in a vertical direction, a left side surface, and a right side surface spaced from the left side surface in a lateral direction that is perpendicular to the vertical direction, the body further defining at least a section of the upper body surface that is continuous along a straight line in the lateral direction from the left side surface to the right side surface,
      wherein the body is configured such that when the intervertebral implant is inserted into the intervertebral space, 1) each of the upper body surface and the lower body surface is disposed within the intervertebral space from the front body surface to the rear body surface, 2) a majority of the upper body surface contacts an endplate of a first vertebral body, and 3) a majority of the lower body surface contacts an endplate of a second vertebral body, the majority of the lower body surface spaced from the majority of the upper body surface a first vertical distance with respect to the vertical direction;
   (b) a plate comprising a biocompatible non-bone material, the plate defining a front plate surface, a rear plate surface opposite the front plate surface, an upper plate surface, a lower plate surface opposite the upper plate surface, at least one plate hole having a first opening in the front plate surface, and a recess having a second opening in the front plate surface, the first opening and the second opening being open to each other, the plate configured such that when the intervertebral implant is inserted into the intervertebral space each of the upper plate surface and the lower plate surface is disposed within the intervertebral space from the front plate surface to the rear plate surface,
      wherein the plate is configured to be mounted to the body such that the rear plate surface faces the front body surface, the first opening is positioned between the left side surface and the right side surface, and the plate is devoid of any screw holes with an opening that has a center that is spaced from either the upper body surface or the lower body surface by a vertical distance greater than the first vertical distance with respect to the vertical direction, the opening disposed at the front plate surface;

(c) at least one bone fixation element configured to be inserted in a first direction through the at least one plate hole and into the endplate of a respective one of the first and second vertebral bodies; and (d) a securing element configured to be inserted into the recess, such that the securing element at least partially covers the first opening to prevent the at least one bone fixation element from exiting the at least one plate hole in a second direction opposite the first direction once the at least one bone fixation element has been driven into the at least one plate hole.

2. The intervertebral implant according to claim 1, wherein the body further comprises teeth protruding from the upper body surface or the lower body surface.

3. The intervertebral implant according to claim 1, wherein the securing element is a plate.

4. The intervertebral implant according to claim 1, wherein the at least one bone fixation element extends along a central axis, and the body defines a horizontal middle plane located between the upper body surface and the lower body surface, and the central axis is oriented at an oblique angle with respect to the horizontal middle plane when the plate is mounted to the body and the at least one bone fixation element is at least partially disposed in one of the at least one plate holes.

5. The intervertebral implant according to claim 4, wherein the oblique angle ranges between 20 degrees and 60 degrees.

6. The intervertebral implant according to claim 4, wherein the oblique angle ranges between 36 degrees and 48 degrees.

7. The intervertebral implant according to claim 4, wherein the oblique angle is 42 degrees.

8. The intervertebral implant according to claim 1, wherein the at least one bone fixation element extends along a respective central axis, and the body defines a vertical middle plane extending from the front body surface to the rear body surface, and the central axis of the at least one bone fixation element is oriented at an oblique angle with respect to the vertical middle plane when the plate is mounted to the body and the at least one bone fixation element is at least partially disposed in one of the at least one plate holes.

9. The intervertebral implant according to claim 8, wherein the oblique angle ranges between 10 degrees and 45 degrees.

10. The intervertebral implant according to claim 1, wherein the body defines a body hole that is disposed closer to the upper body surface than the lower body surface.

11. The intervertebral implant according to claim 10, wherein the body hole is a first body hole, and the body defines a second body hole that is disposed closer to the lower body surface than the upper body surface.

12. The intervertebral implant according to claim 11, wherein the left side surface is connected between the front body surface and the rear body surface, and the right side surface is connected between the front body surface and the rear body surface.

13. The intervertebral implant according to claim 12, wherein neither the first nor the second body hole extends through the left side surface.

14. The intervertebral implant according to claim 12, wherein neither the first nor the second body hole extends through the right side surface.

15. The intervertebral implant according to claim 1, wherein the body is made of a first material, and the plate is made of a second material that is different from the first material.

16. The intervertebral implant according to claim 15, wherein the first material comprises a biocompatible plastic.

17. The intervertebral implant according to claim 15, wherein the second material comprises a metal.

18. The intervertebral implant according to claim 1, wherein the at least one bone fixation element comprises a bone screw.

19. The intervertebral implant according to claim 18, wherein the bone screw comprises a head, a tip, and a shaft connected between the head and the tip.

20. The intervertebral implant according to claim 19, wherein the shaft is externally threaded.

21. The intervertebral implant according to claim 19, wherein a portion of the head of the bone screw is configured to be received in the at least one plate hole.

22. The intervertebral implant according to claim 19, wherein the head of the bone screw is configured to be captured between the plate and the securing element.

23. The intervertebral implant according to claim 1, wherein the plate is mounted the body.

24. The intervertebral implant according to claim 1, wherein the at least one plate hole includes a first plate hole and a second plate hole, and the at least one bone fixation element includes a first bone fixation element and a second bone fixation element, and the securing element at least partially covers the first plate hole and the second plate hole to prevent the first and second bone fixation elements from backing out of the first and second plate holes once the first and second bone fixation elements have been driven into the first and second plate holes.

25. The intervertebral implant according to claim 24, wherein when the first and second bone fixation elements are inserted into the first and second plate holes, the first and second bone fixation elements each extend through the lower body surface.

26. The intervertebral implant according to claim 24, wherein the first plate hole extends toward the upper body surface as the first plate hole extends along a direction from the front plate surface toward the rear plate surface when the plate is mounted to the body.

27. The intervertebral implant according to claim 26, wherein when the first bone fixation element is received within the first plate hole, the first bone fixation element extends into the upper body surface, and when the second bone fixation element is received within the second plate hole, the second bone fixation element extends into the lower body surface.

28. The intervertebral implant according to claim 26, wherein when the first and second bone fixation elements are inserted into the first and second plate holes, the first and second bone fixation elements each extend through the upper body surface.

29. The intervertebral implant according to claim 26, wherein the second plate hole extends toward the lower body surface as the second plate hole extends along a direction from the front plate surface toward the rear plate surface when the plate is mounted to the body.

30. The intervertebral implant according to claim 29, wherein the first bone fixation element comprises a first head and a first shaft connected to the first head, the second bone fixation element comprises a second head and a second shaft connected to the second head, and the first head is disposed closer to the upper body surface than the second head when the first and second bone fixation elements are driven into the first and second plate holes, respectively, and the plate is mounted to the body.

31. The intervertebral implant according to claim 29, further comprising a third bone fixation element, wherein the plate further defines a third plate hole that is configured to receive the third bone fixation element, such that the third bone fixation element extends through the upper body surface when the third bone fixation element is disposed in the third plate hole.

32. The intervertebral implant according to claim 29, wherein the at least one plate hole further includes a third plate hole that is configured to receive a third bone fixation element.

33. The intervertebral implant according to claim 32, wherein the third plate hole extends toward the upper body surface as the third plate hole extends along a direction from the front plate surface toward the rear plate surface when the plate is mounted to the body.

34. The intervertebral implant according to claim 1, wherein the recess extends from the second opening toward the rear plate surface and terminates between the front plate surface and the rear plate surface.

35. The intervertebral implant according to claim 1, wherein at least one of the upper body surface and the lower body surface is convex.

36. An intervertebral implant configured to be inserted into an intervertebral space, the intervertebral implant comprising:
(a) a body defining a front body surface, a rear body surface opposite the front body surface, an upper body surface, a lower body surface spaced from the upper body surface by a first vertical distance with respect to a vertical direction, and opposed side surfaces that are spaced from each other along a lateral direction that is perpendicular to the vertical direction, the body further defining at least one recess that extends from the upper body surface to the lower body surface at a location between the side surfaces, the body further defining a first portion of the upper body surface that is continuous along the lateral direction from one of the opposed side surfaces to the other of the opposed side surfaces,
wherein the body is configured such that when the intervertebral implant is inserted into the intervertebral space, each of the upper body surface and the lower body surface is disposed within the intervertebral space, at least a second portion of the upper body surface contacts an endplate of a first vertebral body, and at least a portion of the lower body surface contacts an endplate of a second vertebral body;
(b) a plate defining an upper plate surface, a lower plate surface opposite the upper plate surface, a front plate surface, a rear plate surface opposite the front plate surface, the plate configured to be mounted to the body such that the rear plate surface faces the front body surface, the plate further defining a plate hole that extends from a first opening to a second opening along a central hole axis that does not pass through the at least one recess when the plate is mounted to the body,
wherein the plate hole is configured to receive a bone fixation element that is driven into the plate hole and into the endplate of one of the first and second vertebral bodies in a first direction, the first opening is disposed in the front plate surface and is positioned between the opposed side surfaces with respect to the lateral direction, the first opening further includes a center that: 1) is spaced from the upper body surface by a second vertical distance with respect to the vertical direction, and 2) is spaced from the lower body surface by third vertical distance with respect to the vertical direction, and both the second vertical distance and the third vertical distances are less than the first vertical distance; and
(c) a securing element configured to be secured to the plate, such that the securing element at least partially covers the first opening to prevent the bone fixation element from exiting the plate hole along a second direction opposite the first direction once the bone fixation element has been driven into the plate hole.

37. The intervertebral implant according to claim 36, wherein the plate includes a plate recess, and the securing element is configured to be received within the plate recess to secure the securing element to the plate.

38. The intervertebral implant according to claim 36, wherein when the plate is mounted to the body, both the body and the plate are configured to be disposed between the endplates of the first and second vertebral bodies at the same time.

39. The intervertebral implant according to claim 36, further comprising the bone fixation element.

40. The intervertebral implant according to claim 39, wherein the bone fixation element extends along a central axis, and the body defines a horizontal middle plane located equidistantly between the upper body surface and the lower body surface, and the central axis is oriented at an angle with respect to the horizontal middle plane when the plate is mounted to the body and the bone fixation element is at least partially disposed in the plate hole.

41. The intervertebral implant according to claim 39, wherein the bone fixation element extends along a central axis, and the body defines a vertical middle plane located between the opposed side surfaces and extending from the front body surface to the rear body surface, and the central axis is oriented at an oblique angle with respect to the vertical middle plane when the plate is mounted to the body and the bone fixation element is at least partially disposed in the plate hole.

42. The intervertebral implant according to claim 36, wherein the body further defines a body hole that is substantially aligned with the plate hole when the plate is mounted to the body, such that the plate hole and the body hole are each configured to receive respective portions of the bone fixation element.

43. The intervertebral implant according to claim 36, wherein the body is made of a first material, and the plate is made of a second material that is different from the first material.

44. The intervertebral implant according to claim 43, wherein the first material comprises a biocompatible plastic.

45. The intervertebral implant according to claim 43, wherein the second material comprises a metal.

46. The intervertebral implant according to claim 36, wherein the body defines a first height measured from the at least a second portion of the upper body surface to the portion of the at least a portion of the lower body surface, and the plate defines a second height measured along the front plate surface from the upper plate surface to the lower plate surface, the second height being substantially equal to the first height.

47. The intervertebral implant according to claim 46, wherein
the body further includes at least one inner surface that extends from the upper body surface to the lower body surface, such that the at least one inner surface defines a periphery of the recess, and the first height is measured along the inner surface from the upper body surface to the lower body surface.

48. The intervertebral implant according to claim 47, wherein the at least one inner surface is positioned between the recess and the front body surface such that the recess is closed with respect to the front body surface.

49. The intervertebral implant according to claim 36, wherein the plate comprises a biocompatible, non-bone material.

50. The intervertebral implant according to claim 36, wherein the second opening is disposed in the rear plate surface.

51. The intervertebral implant according to claim 36, wherein the first vertical distance is defined by 1) the at least a second portion of the upper body surface, and 2) the at least a portion of the lower body surface.

52. The intervertebral implant according to claim 36, wherein the recess is one of a plurality of recesses that are spaced from each other along the lateral direction.

53. An intervertebral implant configured to be inserted into an intervertebral space, the intervertebral implant comprising:
(a) a one-piece body defining a front body surface, a rear body surface opposite the front body surface along a rearward direction, an upper body surface, a lower body surface spaced from the upper body surface in a vertical direction that is perpendicular to the rearward direction, and opposed side surfaces spaced from each other along a lateral direction that is perpendicular to both the rearward direction and the vertical direction,
wherein the body is configured such that when the intervertebral implant is inserted into the intervertebral space, 1) each of the upper body surface and the lower body surface is disposed within the intervertebral space from the front body surface to the rear body surface, 2) a majority of the upper body surface contacts an endplate of a first vertebral body, and 3) a majority of the lower body surface contacts an endplate of a second vertebral body, the majority of the lower body surface spaced from the majority of the upper body surface a first vertical distance with respect to the vertical direction;
(b) a plate comprising a biocompatible non-bone material, the plate defining a front plate surface, a rear plate surface opposite the front plate surface, an upper plate surface, a lower plate surface opposite the upper plate surface, a first plate hole having a first opening in the front plate surface, a second plate hole having a second opening in the front plate surface, a recess having a third opening in the front plate surface, the third opening is open to both the first and second openings, wherein the plate is configured such that when the intervertebral implant is inserted into the intervertebral space, each of the upper plate surface and the lower plate surface is disposed within the intervertebral space from the front plate surface to the rear plate surface,
wherein the plate is configured to be mounted to the body such that the rear plate surface faces the front body surface, the first opening is positioned between the opposed side surfaces with respect to the lateral direction and aligned with the body with respect to the rearward direction, the second opening is positioned between the opposed side surfaces with respect to the lateral direction and aligned with respect to the body with respect to the rearward direction, the second opening positioned laterally offset with respect to the first opening along the lateral direction, and the plate is devoid of any screw holes with an opening that has a center that is spaced from the either the upper body surface or the lower body surface by a vertical distance greater than the first vertical distance with respect to the vertical direction, the opening disposed at the front plate surface;
(c) a first bone fixation element configured to be inserted through the first plate hole and into the endplate of the first vertebral body in a first direction, a second bone fixation element configured to be inserted through the second plate hole and into the endplate of the second vertebral body in a second direction; and
(d) a securing element configured to be inserted into the recess, such that the securing element 1) at least partially covers the first opening to prevent the first bone fixation element from exiting the first plate hole along a direction opposite the first direction, and 2) at least partially covers the second opening to prevent the second bone fixation element from exiting the second plate hole along a direction opposite the second direction.

54. The intervertebral implant according to claim 53, wherein the first plate hole extends from the first opening to a fourth opening in the plate along a first hole axis that passes through a center of the first opening and a center of the fourth opening, the second plate hole extends from the second opening to a fifth opening in the plate along a second hole axis that passes through a center of the second opening and a center of the fifth opening, and the first and second hole axes are oblique to each other.

55. The intervertebral implant according to claim 54, wherein the body further defines at least one body recess that extends from the upper body surface to the lower body surface at a location between the side surfaces, and neither the first hole axis, nor the second hole axis passes through the body recess when the plate is mounted to the body.

56. The intervertebral implant according to claim 55, further comprising:
a first side surface of the plate that extends from the front plate surface to the rear plate surface, and further extends from the upper plate surface to the lower plate surface; and
a second side surface of the plate opposite the first side surface along the lateral direction when the plate is mounted to the body, the second side surface extends from the front plate surface to the rear plate surface, and further extends from the upper plate surface to the lower plate surface;
wherein the plate defines a first straight line that extends in the lateral direction from a first point to a second point, and a second straight line that extends in the lateral direction from a third point to a fourth point;
the first point located at the intersection of the first side surface, the front plate surface, and the upper plate surface;
the second point located at the intersection of the second side surface, the front plate surface, and the upper plate surface;
the third point located at the intersection of the first side surface, the front plate surface, and the lower plate surface;
the fourth point located at the intersection of the second side surface, the front plate surface, and the lower plate surface; and
the first opening is positioned such that a center of the first opening is positioned between the first and second straight lines with respect to the vertical direction.

57. The intervertebral implant according to claim 56, wherein the plate comprises a portion that is aligned with the center of the first opening with respect to the vertical direction, and when the plate is mounted to the body the portion is positioned a second vertical distance from the second straight line with respect to the vertical direction, the first straight line is positioned a third vertical distance from the second straight line with respect to the vertical direction, and the second vertical distance is greater than the third vertical distance.

58. The intervertebral implant according to claim 57, wherein the body further defines at least a section of the upper body surface that is continuous along a straight line in the lateral direction from one of the opposed side surfaces to the other of the opposed side surfaces.

* * * * *